United States Patent [19]

Bistrian et al.

[11] Patent Number: 4,810,726
[45] Date of Patent: Mar. 7, 1989

[54] KERNEL OILS AND DISEASE TREATMENT

[75] Inventors: Bruce R. Bistrian, Ipswich; Vigen K. Babayan, Waban; George L. Blackburn, Jamaica Plain, all of Mass.

[73] Assignee: New England Deaconess Hospital Corporation, Boston, Mass.

[21] Appl. No.: 33,346

[22] Filed: Apr. 1, 1987

[51] Int. Cl.[4] .................. A61K 31/23; A61K 31/20
[52] U.S. Cl. .................... 514/552; 514/558; 514/893; 514/938; 514/943
[58] Field of Search .............. 424/195.1; 426/601; 514/78, 552, 558, 893, 938, 943

[56] References Cited

U.S. PATENT DOCUMENTS

| | | | |
|---|---|---|---|
| 3,232,971 | 2/1966 | Stein et al. | 260/410.7 |
| 3,268,340 | 8/1966 | Babayan et al. | 99/118 |
| 3,494,944 | 2/1970 | Seiden | 260/410.7 |
| 3,658,970 | 4/1972 | Carroll et al. | 514/558 |
| 4,521,440 | 6/1985 | Lansbergen | 426/602 |
| 4,528,197 | 7/1985 | Blackburn | 514/552 |
| 4,703,062 | 10/1987 | Blackburn et al. | 514/552 |

OTHER PUBLICATIONS

"Medium-Chain Triglycerides-Their Composition, Preparation, and Application", V. K. Babayan, Stokely-Van Camp, Inc., Indianapolis, Ind., Reprinted from the Journal of the American Oil Chemists Society, vol. 45, No. 1, pp. 23-25.

"Medium-Chain Triglycerides: An Update[1,2]", Andre C. Bach, Sc.D. and Vigen K. Babayan, Ph.D., The American Journal of Clinical Nutrition 36: Nov. 1982, pp. 950-962.

Primary Examiner—John W. Rollins
Attorney, Agent, or Firm—Lahive & Cockfield

[57] ABSTRACT

A method of treating, and a diet composition for treating patients needing a controlled diet, wherein $C_{12}$ fatty acids are the primary fatty acid source. Preferably lauric fats constitute 33-80% of the diet, while LCT's constitute no more than 20%. The lauric fats may be derived from a natural or fractionated kernel oil, selected from a group consisting of babassu oil, coconut oil, cohune oil, palm kernel oil, and tucum oil. A lipid emulsion with diverse additives is described.

12 Claims, 1 Drawing Sheet

KERNEL OILS AND DISEASE TREATMENT

BACKGROUND OF THE INVENTION

In recent years, the saturated fatty acids have been castigated and maligned as contributing to arteriosclerosis and other coronary disease. However, most of the studies on saturated fatty acids have dealt with long chain triglycerides ("LCT"). Fatty acids, whether of animal, vegetable or marine origin, are normally associated with triglycerides as acyl side chains to a glycerine backbone. Fats and oils of animal, vegetable and marine origin are primarily LCT's, which have 14 or greater carbon atoms in the acyl chain, but can range from 4 to 24 carbon atoms.

It has been long known that the kernel oils are composed primarily of fatty acids which have 14 or less carbon atoms in the chain. Coconut oil and palm kernel oil are typical of these kernel oils and represent a class of fats distinct from conventional fats and oils. Approximately two-thirds of the fats in the kernel oils are saturated, and the majority of the fatty acids have 12 carbon atoms or fewer. Over the years, a number of kernel oils, primarily hydrogenated coconut oil, have been cited as atherogenic because of their high saturated fat content. The kernel oils have been considered poor for food and nutritional applications because of their association with saturated LCT's and stearines.

A recent development in fatty acid nutrition has been the acceptability of the medium chain triglycerides ("MCT") which are obtained, primarily, from fractionation of the kernel oils. MCT's are the first fraction out of three in the normal fractionation process. The MCT's are made up of about 1-2% $C_6$, 65-75% $C_8$, 25-35% $C_{10}$ and 1-2% $C_{12}$ fatty acids. For further details on fractionation, see "Medium-chain triglycerides: an update", A. C. Bach and V. K. Babayan, Am. J. Cl. Nut. 36:950-962 (1982).

The nutritional applications and the unique advantages of the MCT's have led to research in physical mixes of MCT's and LCT's as well as the formation of rearranged structured lipids. The structured lipids have MCT's and LCT's on the same triglyceride backbone and have been shown particularly effective for controlled triglyceride nutrition in hypercatabolic mammals. For example, see U.S. Pat. No. 4,528,197 to G. Blackburn.

The kernel oils themselves form naturally occurring structured lipids. Fraction 2 of these kernel oils, which constitutes approximately 50-65% of the total oil, has almost entirely $C_{12}$ or lauric fats. The $C_{12}$ fats are unique because they can be absorbed into the body by either the portal system or the lymphatic system. In contract, the MCT's are absorbed solely by the portal system while the LCT's are absorbed solely by the lymphatic system.

Structured lipids have an absorption pattern which depends on the molar ratios of the medium and long chain fatty acids on the glyceride molecule. The $C_{12}$ fatty acids have the most versatile absorption pattern because of the dual transport mechanism.

Accordingly, an object of the invention is to provide a lipid source, primarily for use in a controlled diet for critically ill patients, which has lauric acid as the primary fatty acid.

Another object of the invention is to provide a lipid emulsion with lauric fats as the primary fatty acid source.

A further object of the invention is to provide a dietary supplement based on naturally occurring kernel oils which acts as a natural structured lipid.

These and other objects and features of the invention will be apparent from the following description and the claims.

SUMMARY OF THE INVENTION

The present invention features a method of treating patients needing a controlled diet, e.g., critically ill patients, with a diet having lauric fats ($C_{12}$ fatty acids) as the primary fatty acid source. Preferably, the lauric fats constitute 33-80% of the diet while LCT's, which are added for essential nutrition, constitute no more than 20%. The lauric fats are preferably derived from a natural or fractionated kernel oil. Preferred kernel oils are selected from a group consisting of babassu oil, coconut oil, cohune oil, palm kernel oil, tucum oil, and fractionated portions thereof.

The invention also features a lipid emulsion comprising 10-30% lipid fraction, an emulsifier, an osmolality modifier, and water. The lipid fraction is formed of 33-80% lauric fats, preferably selected from the natural kernel oils, and fractionated portions thereof. The preferred emulsifier is egg yolk phospholipid, and glycerol also may be added to the emulsion as an osmolality modifier. Other additives may include amino acids, sugars, vitamins, minerals and other ingredients.

BRIEF DESCRIPTION OF THE DRAWING

The sole FIGURE of the drawing is a schematic of the treatment given the rats used in the experiment described in the Example.

DESCRIPTION OF THE PREFERRED EMBODIMENT

Figure 1:
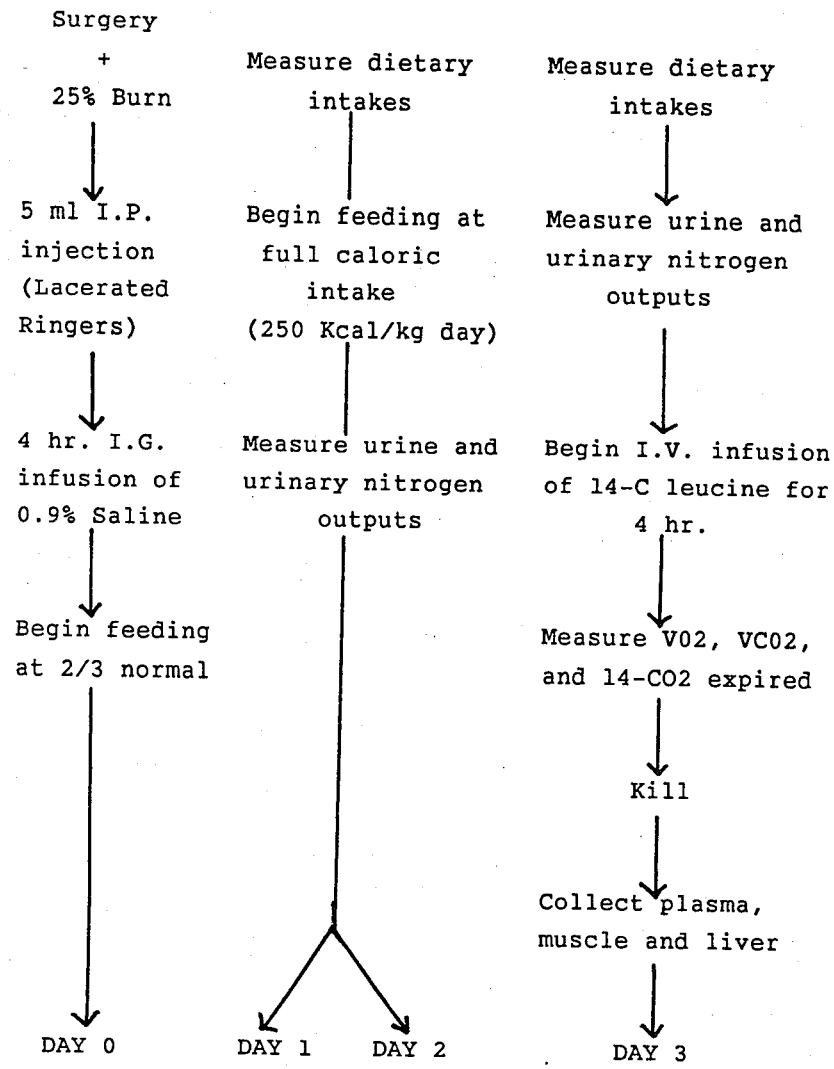

The lauric fats provide surprising nutritional value because of their unique position in intercellular transport mechanisms; that is, they can be absorbed by either the portal or lymphatic systems. The lauric fats provide excellent nutrition for critically ill patients and do not cause any undue coronary difficulties despite their saturation. In fact, the lauric fats provide unexpected usefulness in protein catabolism, yielding positive nitrogen balances and enhanced protein formation.

The following nonlimiting Example will further illustrate the invention.

EXAMPLE

In this Example, the effects of an emulsion rich in lauric fats on a variety of metabolic indicators was determined. The tests used are standards which mimic the effects of diet on patients in metabolic stress, e.g., critically ill patients. Fractions 1 and 2 of palm kernel oil, which contain under 20% MCT's and the remainder lauric fats, were allowed to settle so that the high melting point stearines were removed. The resulting pooled fractions were mixed with 15% soybean oil, which supplied the LCT's necessary for essential nutrition. The controls used in the experiments were soybean (LCT) oil and MCT oil (Captex 300) rich in $C_8$-$C_{10}$ triglyceride. Table 1 gives the compositions of the enteral lipid emulsion used in this Example.

The lipid emulsions were fed to rats which had been catheterized to allow continuous infusion and free movement of the rats. The rats then received a full thickness scald burn injury by immersing 25% of the their body surface in boiling water for 15 seconds. The experimental protocol is further described in U.S. Pat. No. 4,528,197 at column 3, line 30 et seq. and FIG. 1.

The burned and surgically treated rats were divided into three groups, each receiving the same diet except for the identity of the lipid. The diet included 250 kcal/kg/day total caloric intake, 9.8g/AA/kg/day protein intake, 60% of the non-protein calories as dextrose and 40% of the non-protein calories as lipid. Table 2 give the composition of the enteral diets fed each of the three groups.

For Group I, the lipid source was LCT's, a soybean oil. For Group II, the lipid source was MCT's, specifically Captex 300. Group III received the test diet having the fractionated palm kernel oil rich in lauric fats as the lipid source. Twelve rats were used for Group I, 8 rats were used for Group II and 15 rats were used for Group III. All 35 rats survived the three days of enteral feeding.

TABLE 1

| | Composition of Enteral Lipid Emulsions | | |
|---|---|---|---|
| | Control LCT Soybean LCT* | Control Medium Chain Triglyceride Captex 300* | Fractionated Palm Kernel Oil |
| Oil (g/L) | 200 | 200 | 200 |
| Egg yolk phospholipid (g/L) | 12 | 12 | 12 |
| Glycerol (g/L) | 25 | 25 | 25 |
| Water (g/L) | 763 | 763 | 763 |
| Approximate pH** | 7.8 | 7.8 | 7.8 |

20% lipid emulsions were prepared using a Gaulin Homogenizer employing six passes at a second stage/first stage pressure of 500/500 (psi).
*Capital City Products, Columbus, Ohio
**pH adjusted with 0.1 NaOH

TABLE 2

| Composition of Enteral Diets (250 kcal/kg/day) | |
|---|---|
| Amino Acid (g/l)* | 39.0 |
| Dextrose (g/l) | 148.2 |
| Lipid (g/l) | 37.3 |
| Additives | |
| Sodium chloride (mEq/l) | 30 |
| Sodium Acetate (mEq/l) | 30 |
| Potassium Chloride (mEq/l) | 30 |
| Potassium acetate (mEq/l) | 25 |
| Potassium phosphate (mEq/l) | 15 |
| Calcium Gluconate (mEq/l) | 8 |
| Magnesium sulfate (mEq/l) | 8 |
| Trace mineral mix (ml/l)** | 8 |
| Choline chloride (mq/l) | 300 |
| Multivitamin concentrate (ml/l)*** | 5 |

*Crystalline amino acids (Travasol, Baxter-Travenol Laboratories, Deerfield, IL);
**trace mineral mix (Ascot Pharmaceuticals, Inc., Skokie, IL);
***multivitamin concentrate (M.V.C. 9 + 3, Lyphomed, Inc., Melrose Park, IL);
Trace mineral mix (mg/l);
zinc chloride, 16.7; cupric chloride, 8.6; manganese chloride, 2.9; chromic chloride, 0.2; selenious acid, 0.3.
Multivitamin concentrate (per liter): ascorbic acid, 50 mg; retinol, 1650 IU; ergocalciferol, 100 IU; Thiamine, 1.5 mg/riboflavin, 1.8 mg; pyridoxine, 2.0 mg; miacinamide, 20 mg; dexpanthenol, 7.5 mg; di-alpa-tochopherol acetate, 5 IU; biotin, 30 ug; folic acid, 200 ug, cyanocobalamin, 2.5 ug.

TABLE 3

Effect of Thermal Injury on Body Weight Change and Nitrogen Metabolism in Rats

| Group | n | Change in Body Weight (g/3 days) | Nitrogen Balance (mg/day) | | | Cumulative Nitrogen Balance (mg/day 1 + 2) |
|---|---|---|---|---|---|---|
| | | | Day 0 | Day 1 | Day 2 | |
| LCT | 12 | −13.9 ± 1.6 | −119 ± 9 | −5 ± 6 | −7 ± 6 | −12 ± 9 |
| MCT | 8 | −15.1 ± 1.2 | −124 ± 17 | −17 ± 11 | −11 ± 10 | −29 ± 20 |
| Fract. Palm Kernel | 15 | −16.9 ± 1.1 | −98 ± 8 | 15 ± 5* | 22 ± 8** | 37 ± 11** |

Values are means ± SE
n = number of rats
*P 0.05, fract. Palm Kernel vs MCT
**P 0.05, fract. Palm Kernel vs MCT and LCT

TABLE 4

Muscle and Liver Fractional Synthetic Rates (ESR) and Protein Synthesis in Enterally Fed Burned Rats

| Group | n | Muscle | | Liver | |
|---|---|---|---|---|---|
| | | FSR (%/day) | Protein synthesis | FSR (%/day) | Protein synthesis |
| LCT | 9 | 2.4 ± 0.1 | 2.6 ± 0.2 | 31.1 ± 3.4 | 41.4 ± 4.7 |
| MCT | 8 | 2.6 ± 0.1 | 2.6 ± 0.1 | 28.8 ± 1.7 | 38.8 ± 2.5 |
| Fract. Palm Kernel Oil | 8 | 3.2 ± 0.1* | 3.3 ± 0.1 | 45.5 ± 2.7** | 63.7 ± 3.4** |

Values are means ± SE
n = number of rats
a = (umol leucine/g/day)
*P 0.05, Fract. Palm Kernel Oil vs LCT
**P 0.05, Fract. Palm Kernel Oil vs. MCT and LCT

TABLE 5

Whole Body Leucine Kinetics in Enterally Fed Burned Rats

| Group | (n) | Dietary Intake | Release from protein | Appearance | Incorporated into Protein | Oxidation |
|---|---|---|---|---|---|---|
| | | | umol leucine/hr/100 g | | | |
| LCT | 9 | 17.5 ± 1.1 | 17.5 ± 1.1 | 34.9 ± 2.2 | 26.1 ± 1.9 | 8.8 ± 0.7 |
| MCT | 8 | 17.3 ± 0.9 | 17.7 ± 1.1 | 35.0 ± 2.0 | 26.1 ± 1.7 | 8.9 ± 0.7 |
| Fract. Palm Kernel | 8 | 22.0 ± 1.3* | 21.0 ± 1.2 | 43.2 ± 2.4$^a$ | 32.3 ± 1.8 | 10.9 ± 1.1 |

Vaues are means ± SE
n = number of rats
*P 0.05, fract. Palm Kernel vs LCT and MCT
$^a$P 0.05, fract. Palm Kernel vs LCT Table 3 sets forth the effect of diet and thermal injury on body weight change and nitrogen metabolic balance in rats. As is shown by Table 3, all three groups of rats had a loss in body weight over three days, with the largest loss being in Group III, the group receiving the fractionated palm kernel oil. However, since the rats initially weighted approximately 200g each, the difference in weight loss is not significant.

Table 3 also provides the change in nitrogen balance for the three groups. Nitrogen balance was calculated based on total urinary nitrogen excretion and calculated nitrogen input. The nitrogen in the urine was detected using a spectrophotometer and the change measured. As is evident from the Table, all three groups had a negative nitrogen balance on day 0 but only the group receiving the lauric fats, Group III, obtained a positive nitrogen balance any time during the experiment. This positive nitrogen balance is unexpected and shows an increase in protein formation by feeding a diet rich in lipid rather than protein.

Table 4 discloses the fractional synthetic rates and protein synthesis levels in both muscle and liver in the rats after three days feeding with the lipid-based emulsion. A $C^{14}$ leucine tracer was included as part of the amino acids and the amount of leucine in breath and plasma was measured. The fractional synthetic rate, which was calculated using the equation of Garlick et al., and the protein synthesis level are both measures of incorporation of the radioactively labeled leucine into muscle and liver tissue. As is evident from Table 4, the Group III rats, which were fed the palm kernel oil, had much higher rates of leucine incorporation than the other groups. The significance of the higher leucine incorporation is that new protein is being formed at a higher rate in the Group III rats, a confirmation of the positive nitrogen balance.

Table 5 shows the whole body leucine kinetics for the three groups. Although the oxidation rate for the Group III rats was higher, the significant factor is the much higher incorporation of radioactive leucine into protein. Again, this confirms that the rats fed the diet high in lauric fats are forming protein at a significantly higher rate than the rats fed either LCT's or MCT's.

Although the experiments set forth herein were run with fractionated palm kernel oil, similar experiments were run and parallel results obtained with coconut oil and babassu oil. Therefore, the positive effects of the lauric fats can be shown with any of the kernel oils.

As is evident from this Example, feeding a diet rich in lauric fats unexpectedly causes an increase in protein production. The significance of this increase in protein production in the care of critically ill patients is that high protein formation rates should assist in enhancing recovery. Further, this does not require a diet high in protein with its attendant problems.

Although LCT's were included in the diet, their only significance is to supply essential fatty acids needed for proper body function. If it is preferred not to give LCT's, the emulsion of the invention makes this possible.

The methods of the invention are directed to treating patients needing diets with controlled lipid intake and are particularly well suited to post-surgery and other critically ill patients. The emulsion could be used, however, for any lipid controlled diet.

Others skilled in the art may determine modifications and variations which were equivalent to the disclosed invention. Such are the modifications and variations are included in the scope of the following claims.

What is claimed is:

1. A method of treating patients needing diets with controlled lipid intake comprising the step of administering a diet having a lipid source in the form of triglycerides wherein the primary fatty acid in said lipid source is lauric acid.

2. The method of claim 1 wherein said lipid source comprises no more than 20% long chain triglycerides.

3. The method of claim 1 wherein said controlled lipid source comprises 33-80% lauric fats.

4. The method of claim 3 wherein said triglycerides are derived from a natural kernel oil.

5. The method of claim 4 wherein said naturally occurring kernel oil is selected from a group consisting of babassu oil, coconut oil, cohune oil, palm kernel oil, tucum oil, and fractionated portions thereof.

6. The method of claim 1 wherein said patients needing a controlled diet are critically ill patients.

7. The method of claim 1 wherein said diet is administered enterally.

8. The method of claim 1 wherein said diet is administered parenterally.

9. A lipid emulsion including 10-30% lipid fraction, an emulsifier, and water, said lipid fraction comprising 33-80% lauric facts in the form of triglycerides.

10. The lipid emulsion of claim 9 wherein said lipid fraction comprises no more than 20% long chain triglycerides.

11. The lipid emulsion of claim 10 wherein said triglycerides comprises a lauric fat derived from a naturally occurring kernel oil.

12. The lipid emulsion of claim 11 wherein said naturally occurring kernel oil is selected from a group consisting of babassu oil, coconut oil, cohune oil, palm kernel oil, tucum oil, and fractionated portions thereof.

* * * * *